(12) United States Patent
Pazenok et al.

(10) Patent No.: US 9,340,526 B2
(45) Date of Patent: May 17, 2016

(54) PROCESS FOR PREPARING PYRIDYL-SUBSTITUTED PYRAZOLES

(71) Applicant: Bayer Intellectual Property GmbH, Monheim (DE)

(72) Inventors: Sergii Pazenok, Solingen (DE); Norbert Lui, Odenthal (DE); Harry Blaschke, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/665,583

(22) Filed: Mar. 23, 2015

(65) Prior Publication Data

US 2015/0191447 A1 Jul. 9, 2015

Related U.S. Application Data

(62) Division of application No. 13/739,446, filed on Jan. 11, 2013, now Pat. No. 8,987,460, which is a division of application No. 12/753,447, filed on Apr. 2, 2010, now Pat. No. 8,362,261.

(30) Foreign Application Priority Data

Apr. 3, 2009 (EP) .................................. 09157317

(51) Int. Cl.
*C07D 401/04* (2006.01)
(52) U.S. Cl.
CPC ............... *C07D 401/04* (2013.01); *Y02P 20/55* (2015.11)
(58) Field of Classification Search
CPC ..................................................... C07D 401/04
USPC ..................................................... 546/275.4
See application file for complete search history.

(56) References Cited

U.S. PATENT DOCUMENTS

| 8,242,313 B2 | 8/2012 | Pazenok et al. |
| 8,299,260 B2 | 10/2012 | Pazenok et al. |
| 8,362,261 B2 | 1/2013 | Pazenok et al. |
| 8,987,460 B2 | 3/2015 | Pazenok et al. |
| 2006/0183785 A1 | 8/2006 | Chakravarty et al. |
| 2009/0275471 A1 | 11/2009 | Funke et al. |
| 2010/0029478 A1 | 2/2010 | Alig et al. |
| 2011/0021782 A1 | 1/2011 | Pazenok et al. |

FOREIGN PATENT DOCUMENTS

WO    WO 03/016282 A2    2/2003

OTHER PUBLICATIONS

Lahm et al., "Rynaxypyr: A new, etc.," Bioorganic & Medicinal Chemistry Letters 17 (2007) 6274-6279.*
Adamo, M.F.A., et al., "Practical routes to diacetylenic ketones and their application for the preparation of alkynyl substituted pyridines, pyrimidines and pyrazoles," *Tetrahedron 59*:2197-2205, Elsevier Science Ltd., United Kingdom (2003).
Bishop, B.C., et al., "Regioselective Synthesis of 1,3,5-Substituted Pyrazoles from Acetylenic Ketones and Hydrazines," *Synthesis*:43-52, Georg Thieme Verlag Stuttgart, United States (2004).
Liang, J.T., et al., "Design of Concise, Scalable Route to a Cholecystokinin 1 (CCK 1) Receptor Antagonist," *J. Org. Chem. 72*:8243-8250, American Chemical Society, United States (2007).
Martins, M.A.P., et al., "Synthesis of new halo-containing acetylenes and their application to the synthesis of azoles," *Tetrahedron Letters 45*:4935-4938, Elsevier Ltd., United Kingdom (2004).

\* cited by examiner

*Primary Examiner* — Patricia L Morris
(74) *Attorney, Agent, or Firm* — Sterne, Kessler, Goldstein & Fox P.L.L.C.

(57) ABSTRACT

The present invention relates to a process for preparing 1-pyridyl-substituted pyrazoles, comprising the reaction of acetyleneketones with pyridylhydrazine derivatives to give 1-pyridyl-substituted dihydro-1H-pyrazoles, the further reaction thereof with elimination of water to give 1-pyridyl-substituted trihalomethylpyrazoles, and the further processing thereof.

1 Claim, No Drawings

PROCESS FOR PREPARING PYRIDYL-SUBSTITUTED PYRAZOLES

The present invention relates to a process for preparing 1-pyridyl-substituted pyrazoles, comprising the reaction of acetyleneketones with hydrazine derivatives to give 1-pyridyl-substituted dihydro-1H-pyrazoles, the further reaction thereof with elimination of water to give 1-pyridyl-substituted trihalomethylpyrazoles, and the further processing thereof 1-Pyridyl-substituted pyrazoles and dihydro-1H-pyrazoles are valuable intermediates for preparation of anthranilamides, which can find use as insecticides.

The literature has already described the formation of pyrazoles by reaction of 1,3-dicarbonyls or corresponding 1,3-bis-electrophilic reagents with monoalkyl- or arylhydrazines (Synthesis 2004, N1. pp 43-52). However, it is reported that, in the case of monoalkyl- or monoarylhydrazines, the result is a mixture of regioisomeric pyrazoles (Tetrahedron 59 (2003), 2197-2205; Martins at al., T. L. 45 (2004) 4935). Attempts to obtain exclusively one regioisomer failed (JOC 2007, 72822 8243-8250). Likewise described in the literature is a process for preparing trifluoromethylpyrazoles (WO 2003/016282). Likewise described are preparation processes for (het)aryl-substituted pyrazoles (WO 2007/144100), wherein the corresponding pyrazoles are obtained by reducing diesters with DIBAL or LiAlH$_4$. However, very low temperatures are required, and the use of DIBAL is uneconomic.

It is therefore an object of the present invention to provide novel, economically viable processes for preparing 1-pyridyl-substituted pyrazole derivatives and 1-pyridyl-substituted dihydro-1H-pyrazoles, which do not have the disadvantages described above.

The object was achieved in accordance with the invention by a process for preparing pyridyl-substituted pyrazole derivatives of the general formula (I)

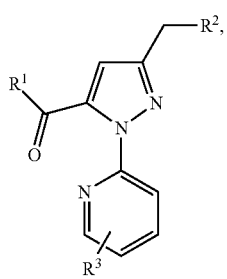

(I)

in which
$R^1$ is alkoxy, hydroxyl, aryloxy, alkylaryloxy, alkyl, cycloalkyl, halogen,
$R^2$ is hydroxyl, alkoxy, arylalkoxy, alkylthio, chlorine, bromine, fluorine, iodine, O—(C=O)alkyl, O—(C=O)O-alkyl, OSO$_2$alkyl, OSO$_2$Ph, OSO$_2$-haloalkyl, OSO$_2$-aryl,
characterized in that
acetyleneketones of the formula (II)

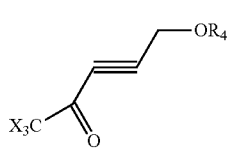

(II)

in which
$R^4$ is a protecting group selected from (C$_1$-C$_6$)-alkyl, aryl, benzyl, tetrahydropyran, (C=O)-alkyl, (C=O)—O-alkyl, Si(alkyl)$_3$.
and X is halogen
are reacted with hydrazinopyridines of the formula (III)

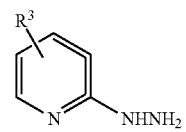

(III)

in which
$R^3$ is halogen, CN, NO$_2$, alkyl, cycloalkyl, haloalkyl, halocycloalkyl, alkoxy, haloalkoxy, alkylamino, dialkylamino, cycloalkylamino,
to give 1-pyridyl-substituted dihydro-1H-pyrazoles of the formula (IV)

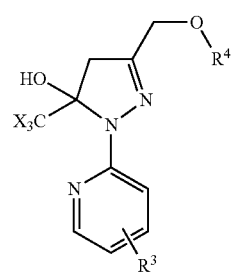

(IV)

in which X, $R^3$, $R^4$ are each as defined above,
the latter are optionally converted further, without preceding isolation, with elimination of water, to 1-pyridyl-substituted trihalomethylpyrazoles of the formula (V)

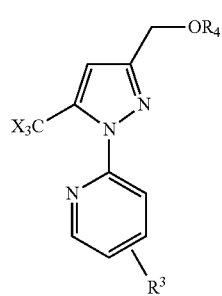

(V)

in which X, $R^3$, $R^4$ are each as defined above,
these compounds of the general formula (V)
are converted with addition of H$_2$SO$_4$, for example, to pyrazolecarboxylic acids of the formula (VI)

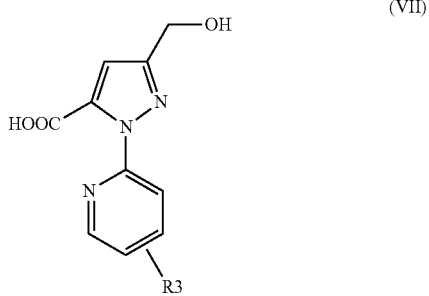

in which $R^3$, $R^4$ are each as defined above,
the latter are converted, after detaching the protecting group $R^4$, to hydroxymethylpyrazole acids of the formula (VII)

(VII)

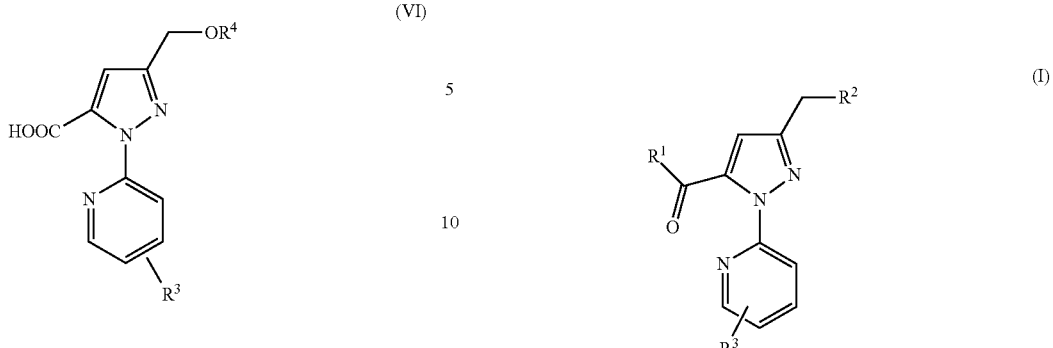

in which $R^3$ is as defined above,
and the latter are converted to compounds of the formula (I).

Surprisingly, a regioselective reaction of acetyleneketones of the formula (II) with hydrazinopyridines of the formula (III) is observed, such that the disadvantages reported in the prior art are not observed. For example, the reaction of 5-(alkoxy or benzyloxy)-1,1,1-trichloropent-3-yn-2-ones with hydrazinepyridine affords, in high yield, only the desired 3-[benzyloxymethyl]-1-(3-chloropyridin-2-yl)-5-(trichloromethyl)-4,5-dihydro-1H-pyrazol-5-ol or 3-[methyloxymethyl]-1-(3-chloropyridin-2-yl)-5-(trichloromethyl)-4,5-dihydro-1H-pyrazol-5-ol.

The process according to the invention can be illustrated by the following scheme (I):

Scheme (I)

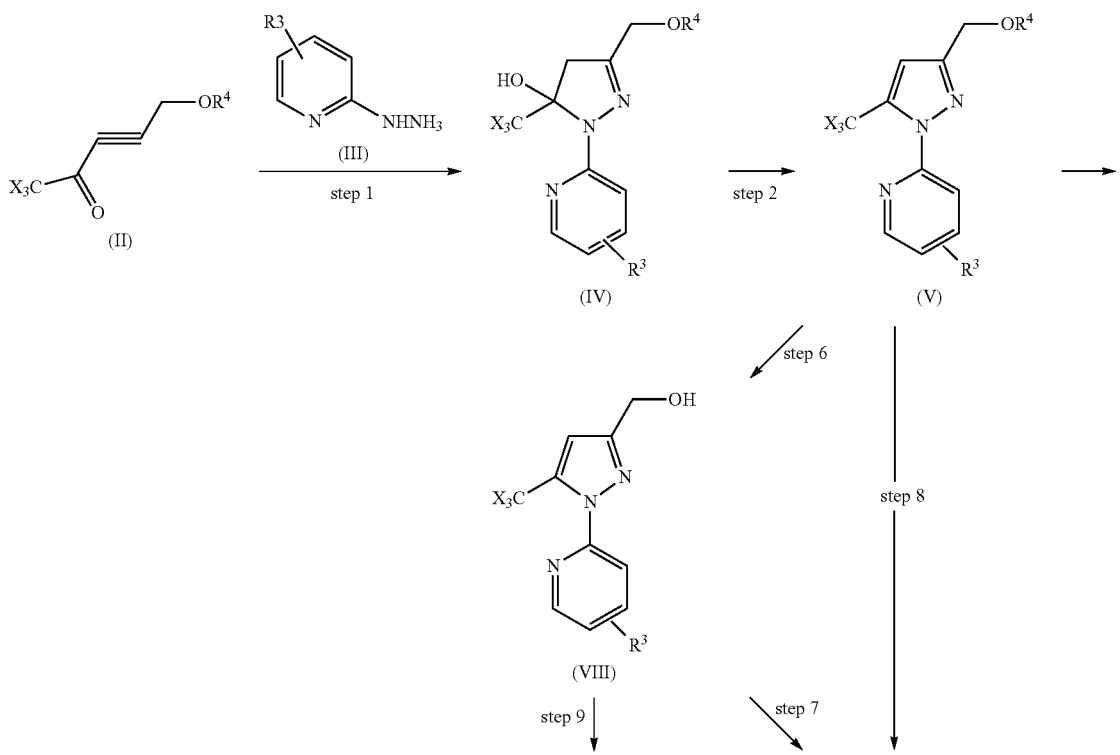

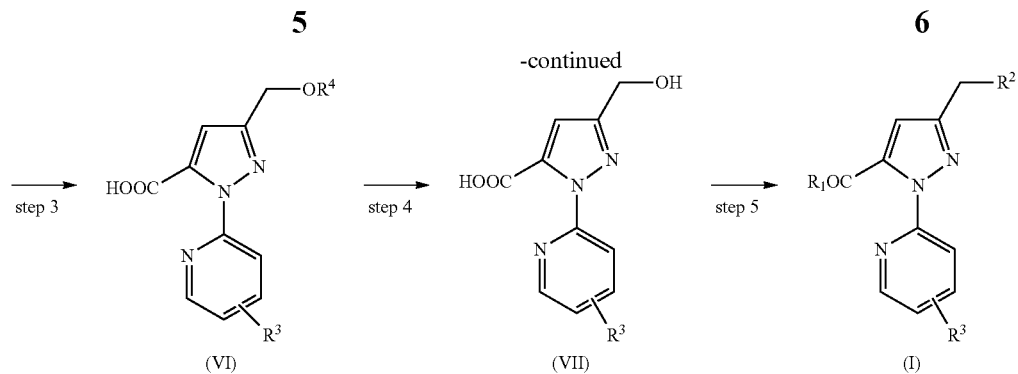

The conversion of a compound of the formula (VII) to a compound of the formula (I) is illustrated by way of example using the following scheme (II).

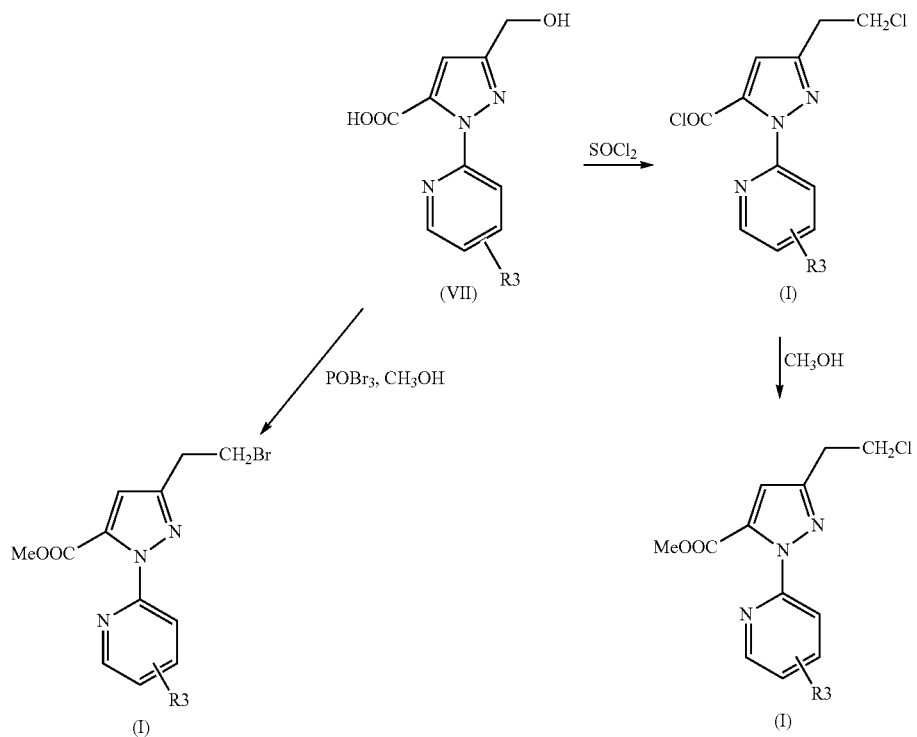

where $R^3$ is as defined above.
Scheme (II)

GENERAL DEFINITIONS

In connection with the present invention, the term "halogens" (X), unless defined otherwise, comprises those elements which are selected from the group consisting of fluorine, chlorine, bromine and iodine, preference being given to using fluorine, chlorine and bromine, and particular preference to using fluorine and chlorine. Substituted groups may be mono- or polysubstituted, and the substituents may be the same or different in the case of polysubstitutions.

Alkyl groups substituted by one or more halogen atoms (—X) (=haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

In connection with the present invention, alkyl groups, unless defined differently, are linear or branched hydrocarbon groups.

The definitions of alkyl and $C_1$-$C_{12}$-alkyl encompass, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In connection with the present invention, unless defined differently, cycloalkyl groups are cyclic saturated hydrocarbon groups.

In connection with the present invention, unless defined differently, arylalkyl groups and arylalkoxy groups are alkyl or alkoxy groups which are substituted by aryl groups and may have an alkylene chain. Specifically, the definition of arylalkyl encompasses, for example, the meanings of benzyl and phenylethyl, and the definition of arylalkoxy, for example, the meaning of benzyloxy.

In connection with the present invention, unless defined differently, alkylaryl groups (alkaryl groups) and alkylaryloxy groups are aryl groups or aryloxy groups which are substituted by alkyl groups and may have a $C_{1-8}$-alkylene chain and may have, in the aryl skeleton or aryloxy skeleton, one or more heteroatoms which are selected from O, N, P and S.

The inventive compounds may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

Propargyl Ether of the Formula (II)

The propargyl ethers used as starting materials in the performance of the process according to the invention are defined in general terms by the formula (II)

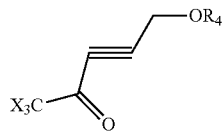

(II)

where X is halogen, preferably fluorine, chlorine or Br, most preferably chlorine,
$R^4$ is a protecting group selected from $(C_1-C_6)$-alkyl, aryl, benzyl, tetrahydropyran, (C=O)-alkyl, (C=O)—Oalkyl, Si(alkyl)$_3$, preferably benzyl, Si(Me)$_3$, phenyl, $(C_1-C_4)$alkyl, (C=O)O-tert-butyl, more preferably $(C_1-C_4)$-alkyl and benzyl and (C=O)O-tert-butyl.

Examples of acetyleneketones of the formula (II) which are suitable in accordance with the invention are
5-(benzyloxy)-1,1,1-trichloropent-3-yn-2-one, 5-(benzyloxy)-1-bromo-1,1-dichloropent-3-yn-2-one, 5-(benzyloxy)-1,1-dichloro-1-fluoropent-3-yn-2-one, 5-(phenyloxy)-1,1,1-trichloropent-3-yn-2-one, 5-(benzyloxy)-1,1,1-trifluoropent-3-yn-2-one, 5-(benzyloxy)-1,1,1-trichloropent-3-yn-2-one, 1,1,1-trichloro-5-(tetrahydro-2H-pyran-2-yloxy)pent-3-yn-2-one, 5-(trimethylsilyloxy)-1,1,1-trichloropent-3-yn-2-one, 5-(methyloxy)-1,1,1-trichloropent-3-yn-2-one.

Processes for preparing acetyleneketones are described in the prior art, for example in THL 45(2004), 4935-4938; JOC 2002, 67, 9200-9209.

Hydrazinopyridines of the General Formula (III)

The hydrazinopyridines used according to the present invention are compounds of the general formula (III)

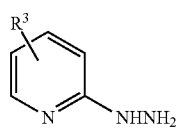

(III)

in which
$R^3$ is halogen, CN, $NO_2$, alkyl, cycloalkyl, haloalkyl, halocycloalkyl, alkoxy, haloalkoxy, alkylamino, dialkylamino, cycloalkylamino,
$R^3$ is preferably halogen, CN, $NO_2$, $(C_1-C_6)$-alkyl, halo$(C_1-C_6)$-alkyl, $(C_1-C_6)$alkoxy, halo$(C_1-C_6)$alkoxy,
$R^3$ is more preferably F, chlorine, bromine, iodine, CN, $(C_1-C_4)$-alkyl, halo$(C_1-C_4)$-alkyl, halo$(C_1-C_4)$alkoxy,
$R^3$ is most preferably fluorine, chlorine, bromine, iodine, especially chlorine.

One example of a hydrazinopyridine suitable in accordance with the invention is 3-chloro-2-hydrazinopyridine.

Step (1)

In a first embodiment of the present process, 2-acylated propargyl ethers of the formula (II) are first reacted with hydrazinopyridines of the formula (III). Thereafter, the intermediates formed in step (1) are converted to the 5-trihalomethylpyrazole derivatives of the formula (V) with elimination of water (step 2).

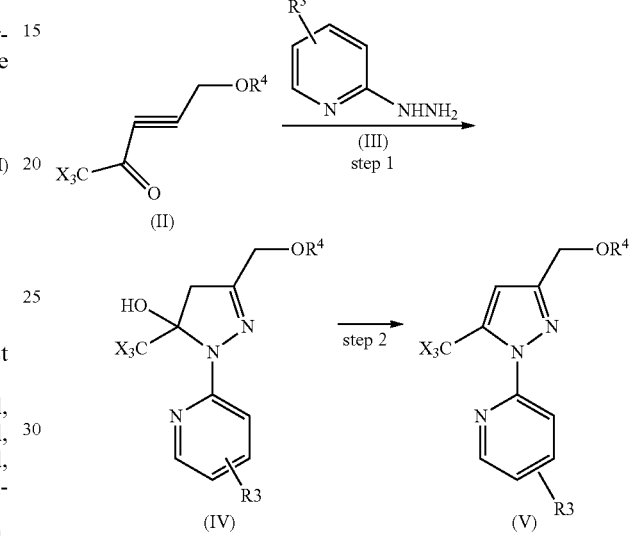

in which X, $R^3$, $R^4$ are each as defined above.

It is considered to be surprising that the cyclization of propargyl ether of the formula (II) with hydrazinopyridines of the formula (III) proceeds with high regioselectivity, such that only the desired regioisomer of the formula (IV) is formed. The compounds of the formulae (IV) and (V) are novel.

Process step (1) of the invention is performed preferably within a temperature range from −20° C. to +100° C., more preferably at temperatures of −10° C. to +70° C.

Process step (1) of the invention is generally performed under standard pressure. Alternatively, it is, however, also possible to work under reduced pressure in order to remove the water.

The reaction time is not critical and may be selected, according to the batch size and temperature, within a range between a few minutes and several hours.

In the performance of the process step of the invention, 1 mol of the propargyl ether of the formula (II) is reacted with 0.8 mol to 1.5 mol, preferably 0.9 mol to 1.2 mol, more preferably with the equimolar amount, of the hydrazinopyridine of the formula (III).

Suitable solvents are, for example, aliphatic, alicyclic or aromatic hydrocarbons, for example petroleum ether, n-hexan, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphoramide; sulphoxides such as dimethyl sulphoxide, or sulphones such as sulpholane, alcohols such as methanol, ethanol, i-propanol. Particular preference is given to using toluene, xylene, chlorobenzene, n-hexane, cyclohexane or methylcyclohexane, ethanol, very particular preference to using toluene, xylene, THF, methyl tert-butyl ether, ethanol, acetonitrile.

The 3-[(alkoxy)methyl]-1-(pyridin-2-yl)-5-(trihaloalkyl)-4,5-dihydro-1H-pyrazol-5-ols formed can be used without preceding workup in the subsequent step (2), in which water is eliminated.

Alternatively, these intermediates can be isolated by suitable workup steps and optionally further purification. It is then possible to eliminate water only at a later stage.

Step 2. Water Elimination

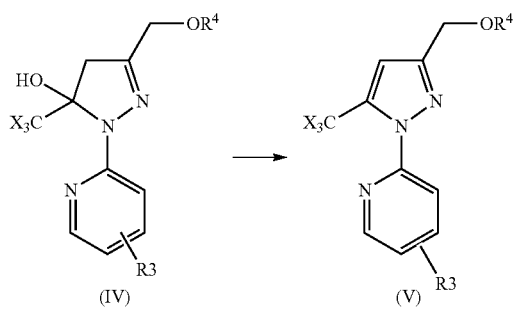

in which X, $R^3$, $R^4$ are each as defined above.

For the water elimination, it is possible, for example, to use the following reagents: $H_2SO_4$, $CF_3COOH$, $(CH_3)_3COCl$, $POCl_3$, polyphosphoric acid, $SOCl_2$, $(CH_3CO)_2O$, $(CF_3CO)_2O$, oxalyl chloride, phosgene, diphosgene.

Particular preference is given to $(CF_3CO)_2O$, oxalyl chloride, thionyl chloride and phosgene.

Process step (2) of the invention is preferably performed within a temperature range from −20° C. to +100° C., more preferably at temperatures of −10° C. to +70° C.

Process step (2) of the invention is generally performed under standard pressure. Alternatively, it is, however, also possible to work under reduced pressure or under elevated pressure (e.g. reaction with phosgene).

The reaction time is not critical and may, depending on the batch size and temperature, be selected within a range between a few minutes and several hours.

In the performance of the process step of the invention, 1 mol of the 3-[(alkoxy)methyl]-1-(pyridin-2-yl)-5-(trihaloalkyl)-4,5-dihydro-1H-pyrazol-5-ol of the formula (IV) is reacted with 0.1 to 2 mol, preferably 0.2 mol to 1.8 mol, more preferably with 0.2-1 mol, of the dewatering agent. It is also possible to perform the elimination of water with catalytic amounts of H2SO4 or CF3COOH.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; ketones such as acetone, methyl ethyl ketone, methyl isobutyl ketone or cyclohexanone; amides such as N,N-dimethylformamide, N,N-dimethylacetamide, N-methylformanilide, N-methylpyrrolidone or hexamethylphosphoramide; sulphoxides such as dimethyl sulphoxide, or sulphones such as sulpholane. Particular preference is given to using toluene, xylene, chlorobenzene, n-hexane, cyclohexane or methylcyclohexane, very particular preference to using toluene, xylene, THF, $CH_2Cl_2$, methyl tert-butyl ether.

Steps 3 and 4

In a further embodiment of the process according to the invention, the trihaloalkylpyrazoles of the formula (V) are converted according to the scheme which follows to the pyrazoles of the formula (VI) or formula (VII). This prepares the alkoxycarboxylic acid of the formula (VI) by hydrolysis of the trihalomethyl group (step 3), then elimination of the protecting group prepares the desired 3-(hydroxymethyl)-1-(pyridin-2-yl)-1H-pyrazole-5-carboxylic acid (step 4).

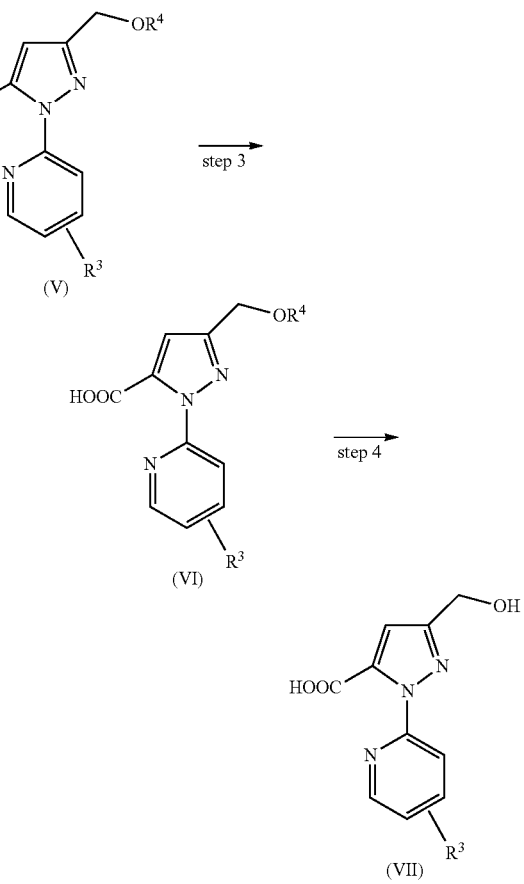

in which X, $R^3$, $R^4$ are each as defined above.

In a preferred embodiment of the process according to the invention, the 2-[3-(alkoxymethyl)-5-(trihalomethyl)-1H-pyrazol-1-yl]pyridine of the formula (V) is converted directly to the 3-(hydroxymethyl)-1-(pyridin-2-yl)-1H-pyrazole-5-carboxylic acid of the formula (VII).

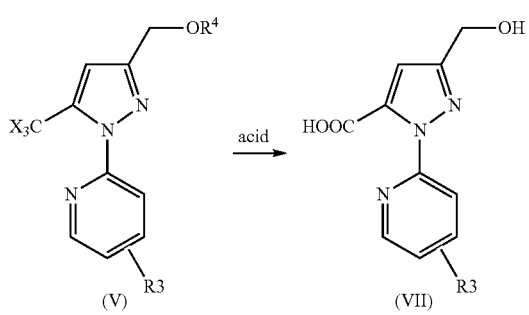

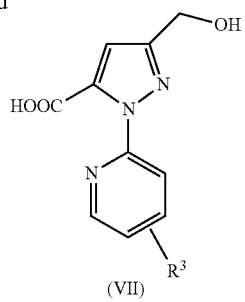

in which X, $R^3$, $R^4$ are each as defined above.

The compounds of the formula (VII) are likewise novel.

The reaction is generally performed under acidic or basic conditions.

Preference is given to mineral acids, for example $H_2SO_4$, HCl, $HSO_3Cl$, HF, HBr, HI, $H_3PO_4$, or organic acids, for example $CF_3COOH$, p-toluenesulphonic acid, methanesulphonic acid, trifluoromethanesulphonic acid.

The reaction can be accelerated by the addition of catalysts, for example $FeCl_3$, $AlCl_3$, $BF_3$, $SbCl_3$, $NaH_2PO_4$.

Basic hydrolysis is effected in the presence of organic bases such as trialkylamines, alkylpyridines, phosphazines and 1,8-diazabicyclo[5.4.0]undecene (DBU), inorganic bases such as alkali metal hydroxides, for example lithium, sodium or potassium hydroxide, alkali metal carbonates ($Na_2CO_3$, $K_2CO_3$) and acetates such as NaOAc, KOAc, LiOAc, alkoxides, for example NaOMe, NaOEt, NaOt-Bu, KOt-Bu.

Steps 6 and 9

In a further embodiment of the process according to the invention, the alkoxy group is first detached (step 6). Subsequently, the hydrolysis of the trihalomethyl group is undertaken (step 9).

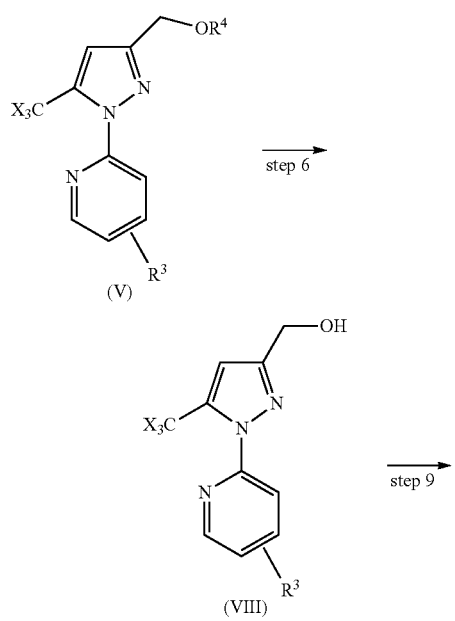

where X and $R^3$ and $R^4$ are each as defined above.

The elimination of the protecting group depends on the definition of the $R^4$ radical. If $R^4$ is ($C_1$-$C_6$)-alkyl or benzyl, the elimination can be effected in the presence of $BBr_3$, HCl, HI, $Me_3SiI$, PyHCl, $FeCl_3$, $BF_3$, and in the case of benzyl additionally by catalytic hydrogenation. Acetyl or alkylsulphonyl groups can be eliminated under basic conditions (NaOH, KOH, $Na_2CO_3$, $NaHCO_3$), and $SiMe_3$ in the presence of F anions.

Step 8.

If $R^4$ is ($C_1$-$C_6$)-alkyl or benzyl, the $CX_3$ group can be converted directly to the ester group. It is thus possible to convert compounds of the formula (V) directly to the compounds of the formula (I) (step 8).

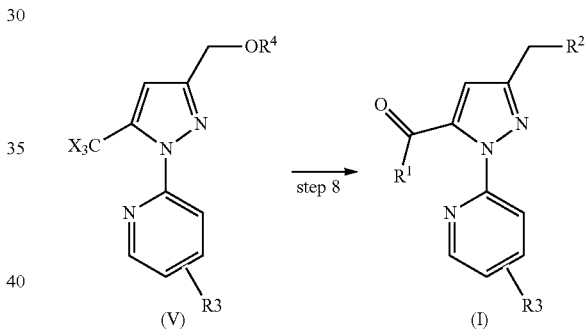

where
X, $R^2$, $R^3$ and $R^4$ are each as defined above,
$R^1$ is ($C_1$-$C_6$)-alkoxy,
$R^1$ is preferably methoxy, ethoxy, propoxy,
$R^2$ is ($C_1$-$C_6$)-alkoxy, aryl($C_1$-$C_6$)-alkoxy,
$R^2$ is preferably ($C_1$-$C_6$)-alkoxy.

For these purposes, for example, alcohols are used, for example methanol, ethanol, propenol, or the alcohol/HCl, alcohol/$FeCl_3$, alcohol/$H_2SO_4$ or alcohol/alkoxide (NaOMe, NaOEt, KOEt, NaOPr) combinations.

Reaction step 8 can be performed in substance or in a solvent. Preference is given to performing the reaction in a solvent. Suitable solvents are, for example, selected from the group consisting of water, aliphatic and aromatic hydrocarbons, for example n-hexane, benzene or toluene, which may be substituted by fluorine and chlorine atoms, such as methylene chloride, dichloroethane, fluorobenzene, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; alcohols such as methanol, ethanol, i-propanol; amides such as dimethylformamide (DMF) or N-methylpyrrolidone (NMP), or mixtures of such solvents, particularly suitable solvents being water, alcohols such as methanol, ethanol, i-propanol, acetonitrile, dichloromethane.

Step 7

In compounds of the formula (VIII), the $CX_3$ group can be converted directly to the ester group. It is thus possible to convert the compounds of the formula (VIII) directly to the compounds of the formula (I) (step 7).

Step 5.

The compounds of the formula (VII) used in the performance of the process according to the invention are converted in a two-stage process to the compounds of the formula (I)

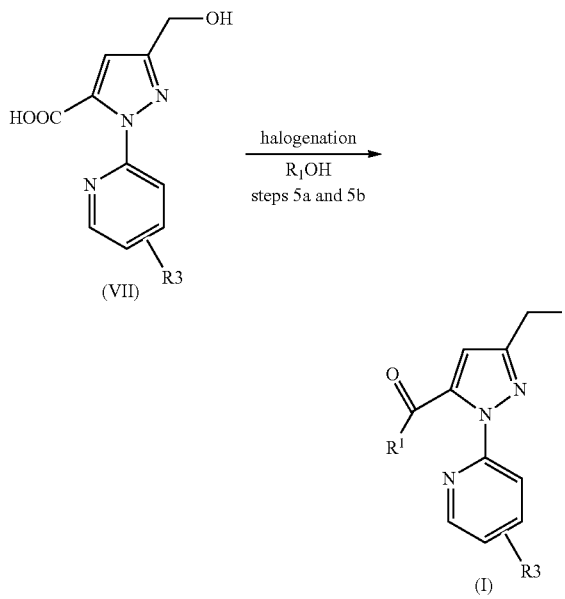

First, the compounds of the formula (VII) are converted with a halogenating agent to the corresponding acid halides. At the same time, the exchange of the hydroxyl group for halogen also takes place.

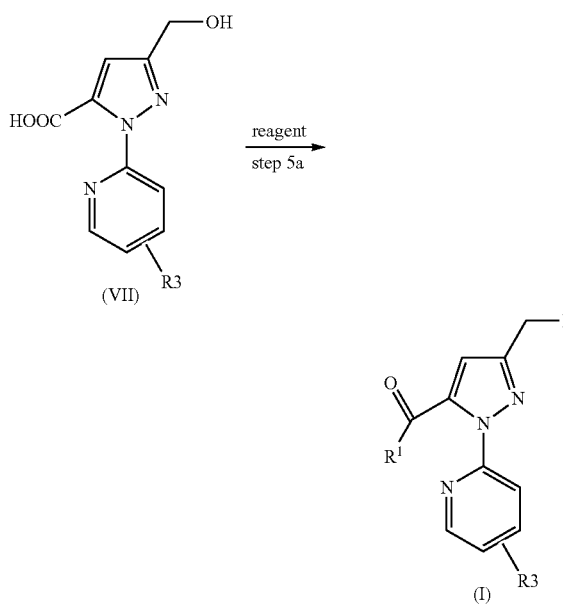

in which $R^1$ is halogen and $R^2$ is chlorine, bromine, iodine, fluorine.

The compounds of the formula (I) in which $R^1$ is halogen and $R^2$ is chlorine, bromine, fluorine, iodine are novel.

To form the acid halides and to exchange hydroxyl for halogen, the following reagents are suitable: $SOCl_2$, $POCl_3$, oxalyl chloride, phosgene, diphosgene, $POBr_3$, $PBr_3$, $SF_4$, $HCF_2CF_2N(Me)_2$, $PI_3$. Preference is given to $SOCl_2$, oxalyl chloride, $POCl_3$, phosgene.

The halogenation step of the invention (step 5a) is performed preferably within a temperature range from $-20°$ C. to $+100°$ C., more preferably at temperatures of $-10°$ C. to $+70°$ C.

The process step of the invention is generally performed under standard pressure. Alternatively, it is, however, also possible to work under reduced pressure or under elevated pressure (e.g. reaction with phosgene).

The reaction time is not critical and may, depending on the batch size and temperature, be selected within a range between a few minutes and several hours.

In the performance of the process step of the invention, 1 mol of the acid of the formula (VII) is reacted with 1.9 mol to 2.5 mol, preferably 195 mol to 2.2 mol, more preferably with the equimolar amount (2 eq), of the chlorinating agent.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide. Particular preference is given to using toluene, xylene, chlorobenzene, n-hexane, cyclohexane or methylcyclohexane, methylene chloride, dichloroethane, very particular preference to using toluene, xylene.

In step 5b, the acid halides react with alcohol to form esters of the formula (I).

Preference is given to the alcohols such as methanol, ethanol, propanol, i-propanol, cyclohexanol.

The process step of the invention is preferably performed within a temperature range from $-20°$ C. to $+100°$ C., more preferably at temperatures of $-10°$ C. to $+40°$ C.

The reaction time is not critical and may, depending on the batch size and temperature, be selected within a range between a few minutes and several hours.

In the performance of the process step of the invention, 1 mol of the acid halide of the formula (VII) is reacted with 1 to 3 eq, preferably 1 eq of the alcohol. The reaction can be performed in alcohol as solvents. The halogenation and reaction with alcohol are generally performed as a one-pot reaction.

The inventive compounds of the formula (I) are valuable intermediates in the synthesis of anthranilamides (WO 2007/112893, WO 2007/144100).

PREPARATION EXAMPLES

Example 1

5-(Benzyloxy)-1,1,1-trichloropent-3-yn-2-one, 5-(Benzyloxy)-1-bromo-1,1-dichloropent-3-yn-2-one were prepared from benzyl propargyl ether, butyl-Li and CCl₃COOEt as described in *THL* 45(2004) 4935-4938.

Example 2

3-[(Benzyloxy)methyl]-1-(3-chloropyridin-2-yl)-5-(trichloromethyl)-4,5-dihydro-1H-pyrazol-5-ol 5-(Benzyloxy)-1,1,1-trichloropent-3-yn-2-one (2.9 g, 0.01 mol) and 3-chloro-2-hydrazinopyridine (1.43 g, 0.01 mol) were initially charged in 20 ml of methyl tert-butyl ether (exothermic), and the mixture was stirred at 30° C. for a further 1 h. The solvent was concentrated by rotary evaporation and the resulting mixture was analysed by means of LC/MS. Only one isomer at m/e 435 was identified. The yield was 94%, the purity 92% (area percent).
Characterization:
$^1$H NMR (CDCl$_3$): 3.5 [(1H, d (19 Hz)]; 3.84 [(1H, d, 19 Hz)]; 4.32 (2H, s); 4.52 (m, 2H), 7.1 (1H, m); 7.3-7.4 (5H, m); 7.8 [(1H, d, 2 Hz)]; 8.1 [(1H, d, 2 Hz)] ppm.
Melting point (m.p.): 112-113° C.

Example 3

1-(3-Chloropyridin-2-yl)-3-[(tetrahydro-2H-pyran-2-yloxy)methyl]-5-(trichloromethyl)-4,5-dihydro-1H-pyrazol-5-ol, mixture of two diastereomers Instead of 5-(benzyloxy)-1,1,1-trichloropent-3-yn-2-one (see Example No. 2), 1,1,1-trichloro-5-(tetrahydro-2H-pyran-2-yloxy)pent-3-yn-2-one was used. The preparation was analogous to that described in Example No. 2.
Characterization of the Resulting Diastereomer Mixture:
$^1$H NMR (CDCl$_3$): 1.46-1.58 (4H); 1.66-1.73 (1H, m); 1.75-1.8 (1H, m); 3.48 (1H, m); 3.81 (1H, m); 3.33 (1H, d); 3.81 (1H, d); 7.21 (1H, dd); 7.23 (1H, dd); 7.94 (1H, dd); 8.22 (1H, dd); 9.48 (1H, bs) ppm.

Example 4

2-{3-[(Benzyloxy)methyl]-5-(trichloromethyl)-1H-pyrazol-1-yl}-3-chloropyridine 4.35 g of 3-[(benzyloxy)methyl]-1-(3-chloropyridin-2-yl)-5-(trichloromethyl)-4,5-dihydro-1H-pyrazol-5-ol were dissolved in 30 ml of methyl isobutyl ether. Then 3 g of trifluoroacetic anhydride were added (exothermic reaction). The mixture was stirred at 25° C. for a further 2 h, in the course of which the precipitate was formed. The precipitate was filtered off and washed. The yield was 95%.
Characterization:
$^1$H NMR (CDCl$_3$): 4.60 (2H, s); 4.62 (m, 2H), 6.95 (1H, s); 7.2-7.4 (5H, m); 7.42 (1H, m); 7.95 [(1H, d, 2 Hz)]; 8.5 [(1H, d, 2 Hz)] ppm.
Melting point (m.p.): 211-213° C.

Example 5

3-[(Benzyloxy)methyl]-1-(3-chloropyridin-2-yl)-1H-pyrazole-5-carboxylic acid 4.4 g of 2-{3-[(benzyloxy)methyl]-5-(trichloromethyl)-1H-pyrazol-yl}-3-chloropyridine and 30 ml of 20% H$_2$SO$_4$ were heated at 100° C. for 24 h.

The precipitate was filtered off and washed with water. The yield was 92%.
Characterization:
$^1$H NMR (CDCl$_3$): 4.61 (2H, s); 4.63 (m, 2H), 6.97 (1H, s); 7.2-7.4 (5H, m); 7.42 (1H, m); 7.96 [(1H, d, 2 Hz)]; 8.5 [(1, d, 2 Hz)] ppm.

Example 6

1-(3-Chloropyridin-2-yl)-3-(hydroxymethyl)-1H-pyrazole-5-carboxylic acid hydrochloride 3.43 g of 3-[(benzyloxy)methyl]-1-(3-chloropyridin-2-yl)-1H-pyrazole-5-carboxylic acid and 20 ml of HCl (37.5%) were heated at 100° C. for 2 h and then the reaction mixture was completely concentrated under reduced pressure at 10 mbar. This gave 1-(3-chloropyridin-2-yl)-3-(hydroxymethyl)-1H-pyrazole-5-carboxylic acid as the hydrochloride. Neutralization with NaHCO$_3$ afforded the free acid as a white solid. The yield was 94%.

Example 7

Methyl 3-(chloromethyl)-1-(3-chloropyridin-2-yl)-1H-pyrazol-5-carboxylate 1-(3-Chloropyridin-2-yl)-3-(hydroxymethyl)-1H-pyrazole-5-carboxylic acid hydrochloride (0.1 mol) was initially charged in 50 ml of toluene. SOCl$_2$ was added in portions at 60° C., The mixture was heated at 70° C. for 3 h, in the course of which the precipitate went completely into the solution. Methanol (30 ml) was slowly added dropwise to the mixture and the solution was stirred at room temperature for one hour. Subsequently, the solution was concentrated under reduced pressure. This afforded 95% of the product with a purity of 96% (area percent).
Characterization
$^1$H NMR (CDCl$_3$): 3.7 (3H, s); 4.7 (2H, s); 7.1 (1H, s); 7.5 (1H, m); 8.05 [(1H, m)]; 8.5 [(1H, m)] ppm.

The invention claimed is:
1. A compound of formula (I)

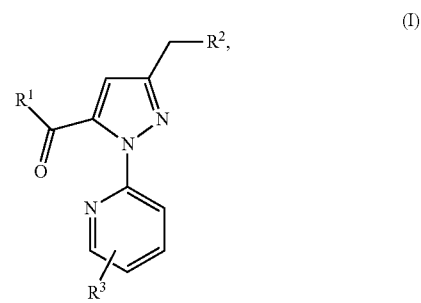

wherein
R$^1$ is halogen,
R$^2$ is fluorine, chlorine, bromine, or iodine, and
R$^3$ is halogen, CN, NO$_2$, alkyl, cycloalkyl, haloalkyl, halocycloalkyl, alkoxy, haloalkoxy, alkylamino, dialkylamino, or cycloalkylamino.

* * * * *